United States Patent
Rennert et al.

[19]

[11] Patent Number: 6,120,481
[45] Date of Patent: *Sep. 19, 2000

[54] SCALE ON A PLASTIC SYRINGE

[75] Inventors: Richard L. Rennert, Kinnelon, N.J.; Charles Goldstein, Chapel Hill, N.C.

[73] Assignee: Becton, Dickinson and Company, Franklin Lakes, N.J.

[*] Notice: This patent issued on a continued prosecution application filed under 37 CFR 1.53(d), and is subject to the twenty year patent term provisions of 35 U.S.C. 154(a)(2).

[21] Appl. No.: 09/217,724

[22] Filed: Dec. 21, 1998

[51] Int. Cl.$^7$ ........................................... A61M 5/00
[52] U.S. Cl. .......................... 604/187; 604/186; 604/189
[58] Field of Search ................................... 604/181, 186, 604/187, 189, 218

[56] References Cited

U.S. PATENT DOCUMENTS

| | | |
|---|---|---|
| Re. 24,322 | 5/1957 | Molinari . |
| 277,213 | 5/1883 | Brinkerhoff . |
| 827,333 | 7/1906 | McElroy et al. . |
| 1,265,537 | 5/1918 | Shull . |
| 1,517,849 | 12/1924 | McLellan . |
| 2,127,043 | 8/1938 | Most ........................................... 18/59 |
| 2,706,496 | 4/1955 | Svenson . |
| 3,325,061 | 6/1967 | Ellsworth ................................ 222/386 |

(List continued on next page.)

OTHER PUBLICATIONS

Sherwood medical, Oral Medication Syringes, Sherwood Medical Product Catalogue, p. 12, Jun. 1990.
Becton and Dickinson, Insulin syringes, BD catalog, p. 22, 1986.
Article entitled "New Developments in Multicomponent Injection Molding" by Richard Wood, pp. 54–55 from Plastics Machinery & Equipment, Sep. 1979.
Article entitled "Multicomponent Injection Molding for Sandwich Construction" by Richard Wood, pp. 16–23 from Plastics Machinery & Equipment, Jan. 1978.
Article entitledCoinjection: New Molding Technology pp. 40–42 from Modern Plastics, Jul. 1976.
Article entitled Innovative Injection Molding Techniques for the Medical Industry by Ken A. Kerouac; Peter F. Grelle, pp. 63–68 from Medical Device & Diagnostic Industry, Apr. 1998.

*Primary Examiner*—John D. Yasko
*Assistant Examiner*—Deborah Blyveis
*Attorney, Agent, or Firm*—Keith J. McWha

[57] ABSTRACT

This invention relates to a medical device having a plastic cylinder that is uniquely decorated. More particularly, this invention relates to an improved scale on a plastic syringe containing protruding volume measuring scale marks and indicia. These protrusions provide tactile sensation of the scale and slip-resistant holding of the syringe barrel. Both the plastic syringe barrel and scale can be formed separately, and then attached to each other. Methods of apply the scale in this manner include overmolding, and heat welding. The plastic syringe and improved scale can also be formed simultaneously using co-injection molding methods. Advantages of forming a scale on the plastic syringe using any of the techniques described above includes eliminating secondary operations such as printing, and permanently and accurately positioning the scale. Different thermoplastic and elastomeric materials and colors can also be used to form the scale. Another advantage is that the scale can be formed to 360° around the cylindrically-shaped plastic syringe barrel. Traditional printing methods like gravure printing are currently unable to achieve this feature.

22 Claims, 7 Drawing Sheets

U.S. PATENT DOCUMENTS

| | | |
|---|---|---|
| 3,656,480 | 4/1972 | Rubricius . |
| 3,885,562 | 5/1975 | Lampkin . |
| 3,923,207 | 12/1975 | Kyogoku . |
| 4,018,223 | 4/1977 | Ethington . |
| 4,181,223 | 1/1980 | Millet . |
| 4,466,426 | 8/1984 | Blackman . |
| 4,666,435 | 5/1987 | Braginetz ................................ 604/198 |
| 4,713,060 | 12/1987 | Riuli ..................................... 604/199 |
| 4,816,021 | 3/1989 | Johnson ................................. 604/110 |
| 5,147,328 | 9/1992 | Dragosits et al. ....................... 604/218 |
| 5,242,405 | 9/1993 | Howe ..................................... 604/125 |
| 5,259,371 | 11/1993 | Tonrey . |
| 5,304,138 | 4/1994 | Mercado ................................. 604/110 |
| 5,320,608 | 6/1994 | Gerrone .................................. 604/117 |
| 5,354,285 | 10/1994 | Mazurik et al. ........................ 604/191 |
| 5,377,879 | 1/1995 | Isaacs ..................................... 222/205 |
| 5,563,356 | 10/1996 | Mussi et al. ........................ 73/864.14 |
| 5,651,774 | 7/1997 | Taranto et al. ........................... 604/198 |
| 5,836,919 | 11/1998 | Skurka et al. ........................... 604/187 |

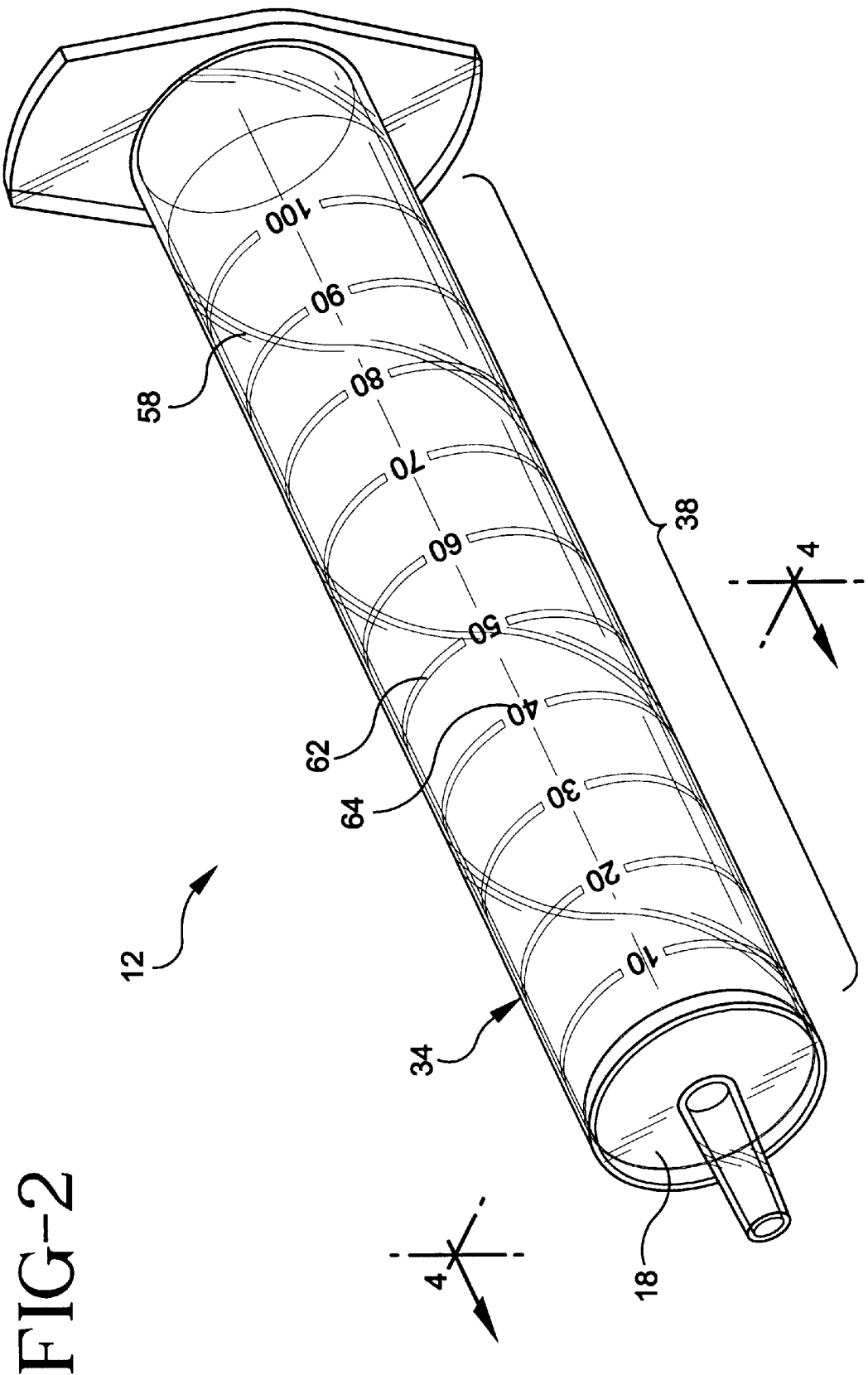

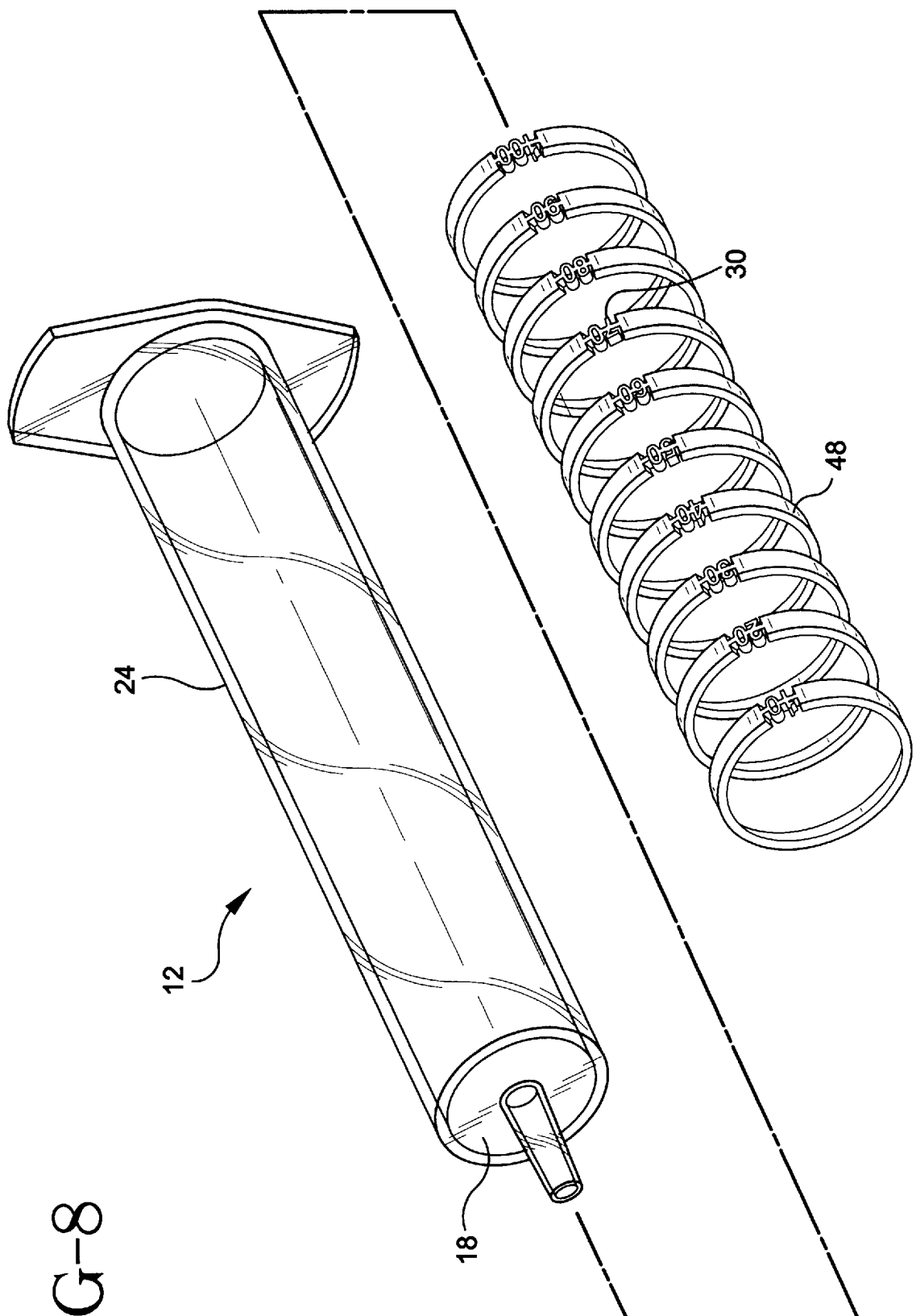

SCALE ON A PLASTIC SYRINGE

BACKGROUND OF THE INVENTION

1. Field of the Invention

This invention relates to a medical device having a plastic cylinder that is uniquely decorated. More particularly, this invention relates to an improved scale on a plastic syringe containing protruding volume measuring scale marks and indicia. These protrusions provide tactile readability of the scale and slip-resistant holding of the syringe barrel.

2. Description of Prior Art

Syringes usually contain volume measuring indicia on the side of the barrel to indicate the volume of liquid contained within the syringe barrel. It is desirable for convenience and preventing medical error to provide volume measuring indicia which are clear and easy to read. The need for readable graphics on a syringe barrel is especially important to diabetics who, after many years of affliction, suffer various side effects such as faulty vision. Diabetics also are believed to suffer from temporary periods of blurred vision. There is also a need to provide slip-resistant holding of the syringe barrel. This need is especially seen in the geriatric patient who self-administers medication. To this end, the scale, scale marks, and volume measuring indicia are important features of the syringe barrel.

There are many ways to manufacture a syringe with a scale. Printing or decorating plastic objects in general with indicia is well known in the art. Flexographic printing is used for printing over films. Offset printing is used for bottles, jars and tubes. Silk-screen printing is used for printing small quantities of parts or for items where an embossed effect is required. Hot stamping is used to engrave the decoration into the plastic part. Hot stamping is best suited for bright or strong colors.

Labeling, such as paper, foil, and fabric can also be used to print or decorate a plastic object. These labels can be printed on by a variety of techniques. The most widely used method of printing on labels is called letterpress. This technique permits good color control, with clear, sharp detail. A variation of this process is called letterset in which the printing is transferred from the plate to a rubber roller and then to the paper or other printed medium. A process called lithography is particularly suited to print on foil. (See Joseph F. Hanlon, *Handbook of Packing Engineering*, 1984, McGraw-Hill, pp. 8.9–8.10 and 12.3–12.8).

Other methods for printing or decorating plastic objects include pad printing where a rubber stamp or tub picks up an image on an ink filled die and transfers the image to the plastic object. Another printing method is called gravure printing. This type of printing is typically used for high volume production.

A common problem with the previously described printing or decorating methods is that they are secondary operations. The syringe must first be manufactured and then the scale is added in a totally different operation or secondary operation. This secondary operation adds cost to the product. Another common problem with the previously described methods is that the printing requires tight precision in positioning the scale on a syringe barrel. In addition, over time, the printing may wear or rub off. Also, certain colors may be limited in each printing or decorating methods. For diabetics with vision problems, a raised scale may be desirable to provide a tactile sensation or tactile readability of the scale and provide slip-resistant holding of the syringe. Current printing techniques that could emboss a scale cannot currently be used in high volume production.

In many printing techniques, like gravure printing, a decoration such as a scale cannot be printed 360° around a cylindrical object. Using a flat foil alone with printed indicia to alleviate this problem has several disadvantages. These disadvantages include the potential of an alignment problem when the foil is wrapped around the plastic object. For a syringe, printing the scale containing the volume measuring indicia from about 1° to about 360° around the syringe would give several advantages. First, it would assist diabetics with vision impairments to correctly read the volume measuring indicia. Second, it would facilitate easier filling and dispensing by the healthcare professional. However, gravure printing techniques, like the other methods previously mentioned, does not allow printing 360° around a cylindrical plastic object like a syringe barrel. Flat foil wrapping techniques would present alignment problems.

Thus, there still remains a need for an improved scale on a plastic syringe barrel that eliminates secondary operations such as printing. This improved method should permanently and accurately position the scale on a plastic syringe barrel. It should also be able to provide a raised scale for tactile sensation or readability and slip-resistant holding of the syringe. Also, it should be adaptable to high volume commercial production. The improved scale would be able to be made in various materials and colors, and it would also have the ability to be printed from about 1° to about 360° around the plastic syringe barrel.

SUMMARY OF THE INVENTION

It is an objective of the present invention to provide a syringe with an improved scale which allows tactile sensation of the scale and slip-resistant holding of the syringe. Another objective of the present invention is to provide an improved scale containing scale marks, and volume measuring indicia that could be accurately and permanently positioned on a plastic syringe barrel thereby eliminating a secondary operation such as printing. Furthermore, it is an objective of the present invention to allow the use of different material and colors to be used on the scale. It is also within the scope of the present invention to provide a scale bar that provides additional support to the scale marks and indicia as well as providing contrast to the scale. In addition, it is an objective of the present invention to allow the improved scale with the volume measuring indicia to be formed from about 1° to about 360° around the plastic syringe barrel. The present invention is adaptable for use in high volume commercial production.

The improved scale on a plastic syringe barrel of the present invention has an elongate barrel. The barrel has transparent inner and outer surfaces. The inner surface forms a chamber that retains the fluid to be injected. A scale is integrally formed into the outer surface of the syringe barrel and is a structural part of the outer surface of the syringe barrel such that the inner surface of the barrel is substantially uninterrupted by the scale. The scale has scale marks and indicia. A scalebar is optional to provide structural support to the scale marks and indicia as well as providing contrast to the scale. The scale does not interrupt the injection of the fluid contained by the inner surface of the syringe barrel. The indicia on the scale are volume measuring indicia. The present invention allows the scale bar to be formed axially along the outer surface of the barrel. The scale marks and indicia are formed from about 1° to 360° circumferentially around the syringe barrel. The scale can be made of an elastomeric material of a color selected from the group consisting of white, black, yellow, red, blue, green and combinations thereof. However, any thermoplastic material can be substituted for the elastomeric material depending on what end product properties are desired. The scale is substantially embedded into the outer surface and can protrude outward giving the user tactile readability of the scale and slip-resistant holding of the syringe.

A few methods of making an improved scale on the syringe barrel that eliminate the need of a secondary printing operation include co-injection molding, heat-welding, and overmolding. Co-injection molding is a multimaterial injection molding technique involving two or more injection units. Heat-welding is a process where two or more materials are bonded together by the application of heat. Overmolding, or two-shot molding is an injection molding process where part of a product is first molded, and the final product is completed when the other part or parts of the product are molded about the first part. In the present invention, an example of the overmolding method would be to first have a tubular foil inserted into an elongate barrel die. The foil is then integrally formed between the inner and outer surfaces of the elongate barrel, such that the inner surface is substantially uninterrupted by the foil, when the elongate barrel is molded around the tubular foil. The tubular foil can be prior injection molded or extruded prior to molding the elongate barrel. The tubular foil has transparent portions in addition to scale marks and indicia. A scale bar is optional and would provide in this embodiment additional contrast to the scale. The indicia is volume measuring indicia. This process would eliminate the need for a secondary printing operation and is also known as in-mold assembly.

BRIEF DESCRIPTION OF THE DRAWINGS

FIG. 2 is a perspective view illustrating an alternative embodiment of the syringe barrel with an improved scale.

FIG. 8 is an exploded perspective of an alternate embodiment of FIG. 1.

DETAILED DESCRIPTION

Figure 1:
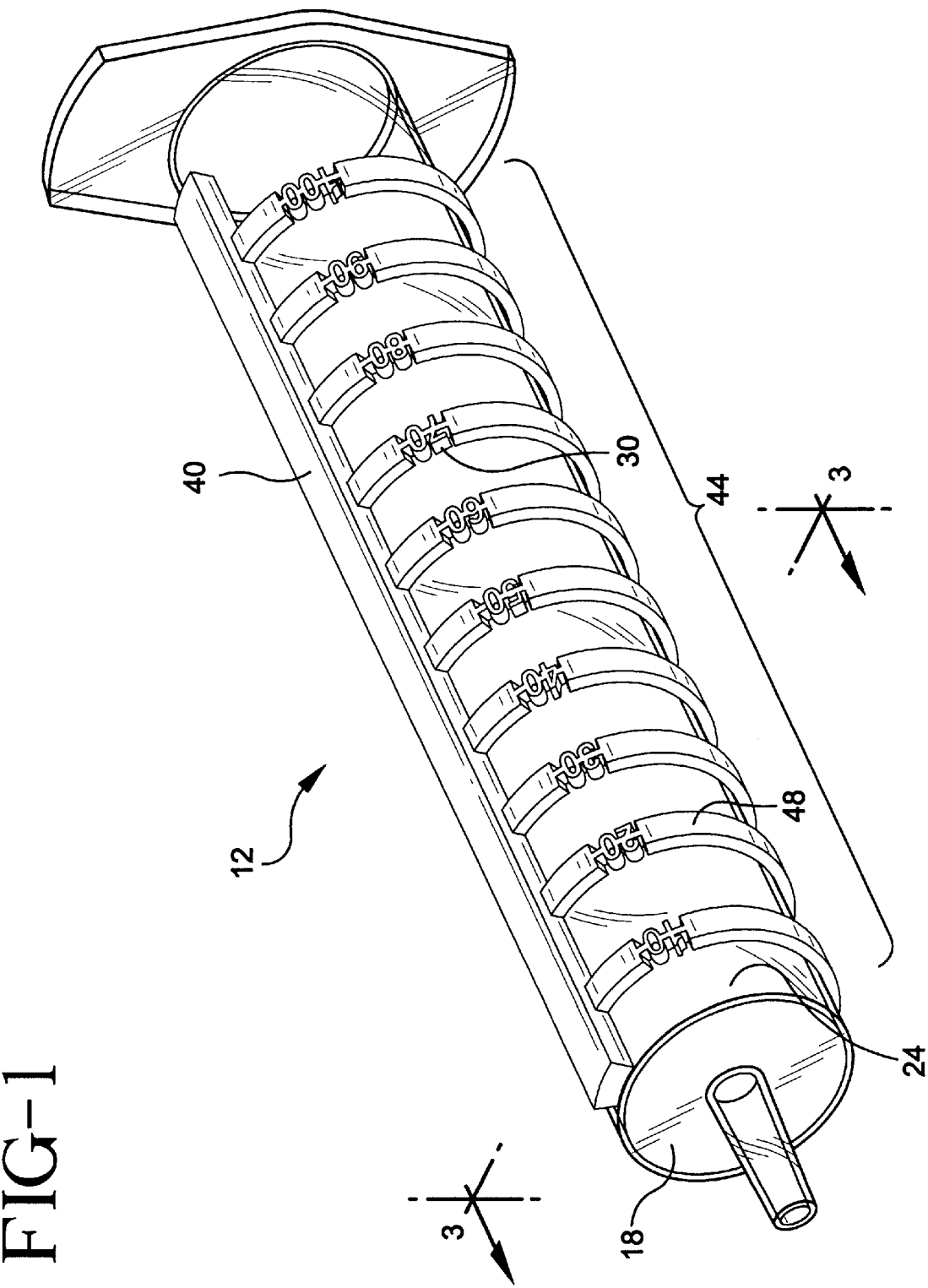
FIG. 1 is a perspective view of the syringe barrel with an improved scale.

While this invention is satisfied by embodiments in many different forms, there are shown in the drawings and will be herein described in detail preferred embodiments of the invention with the understanding that the present disclosure is to be considered exemplary of the principles of the invention. This disclosure is not intended to limit the scope of the invention to the embodiments illustrated. The scope of the invention is outlined by the attached claims and their equivalents.

Figure 3:
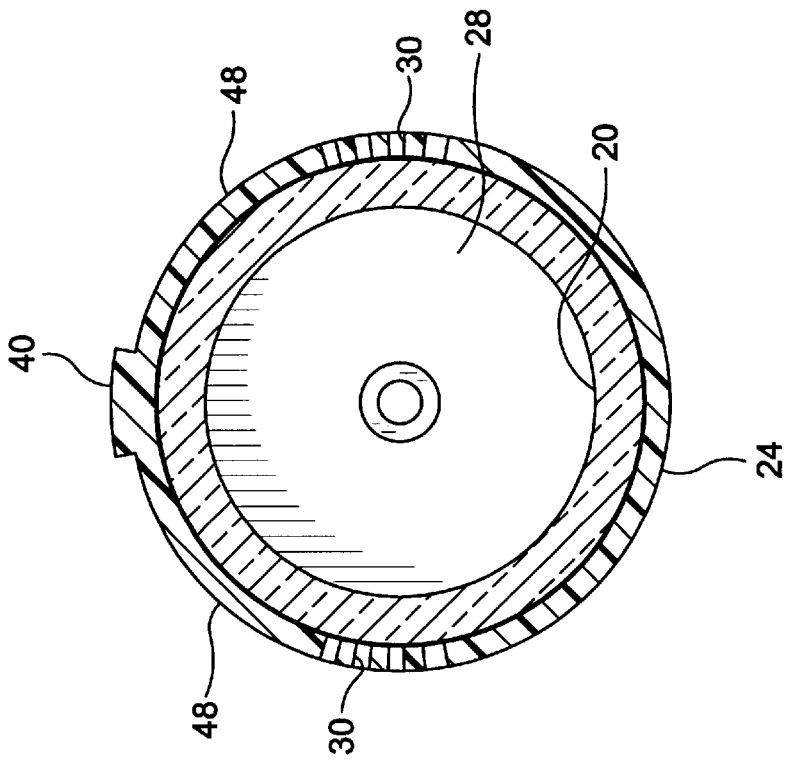
FIG. 3 is a cross-sectional view of the syringe barrel with an improved scale of FIG. 1 taken along lines 3—3.
Figure 5:
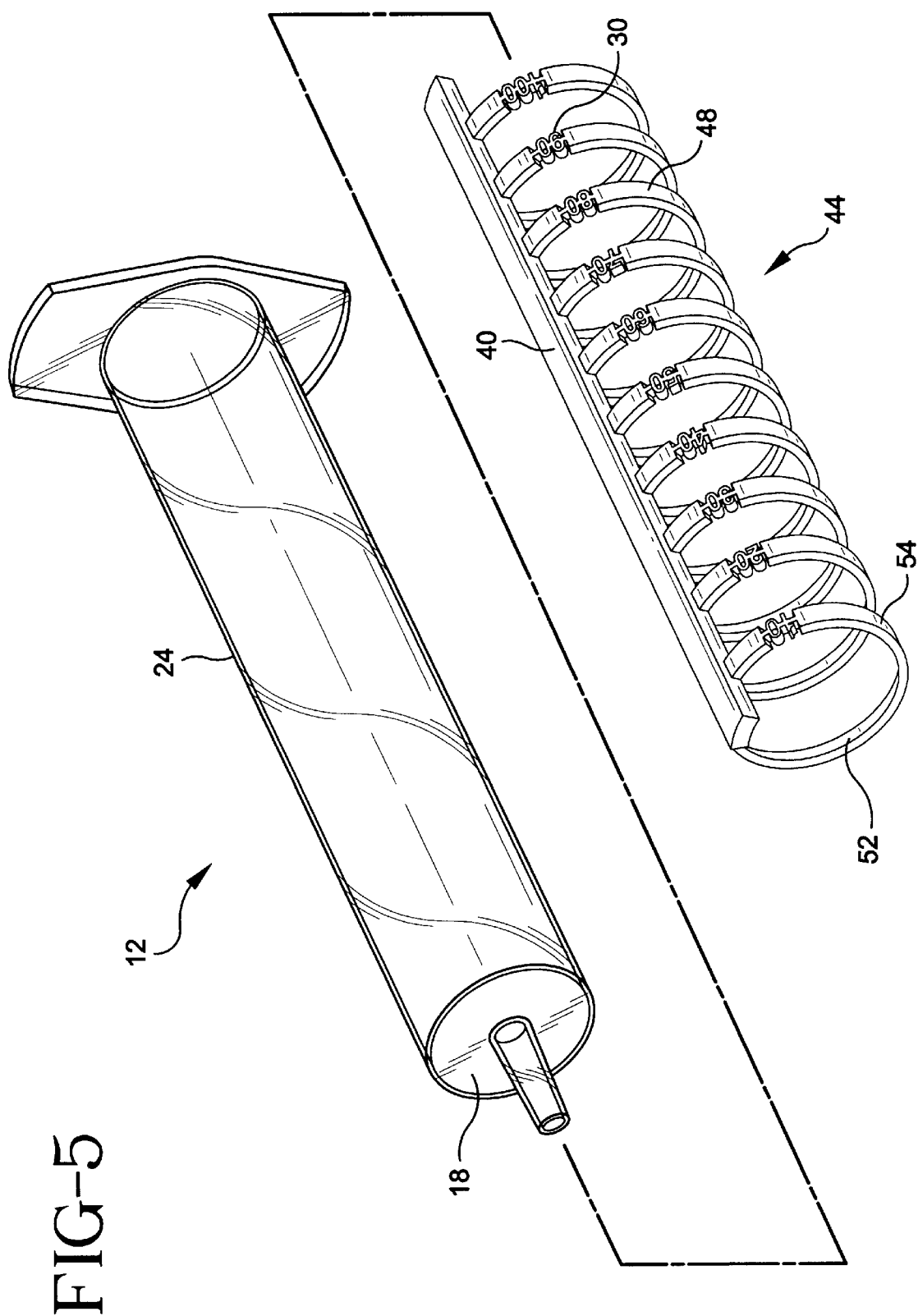
FIG. 5 is an exploded perspective view of FIG. 1.
Figure 6:
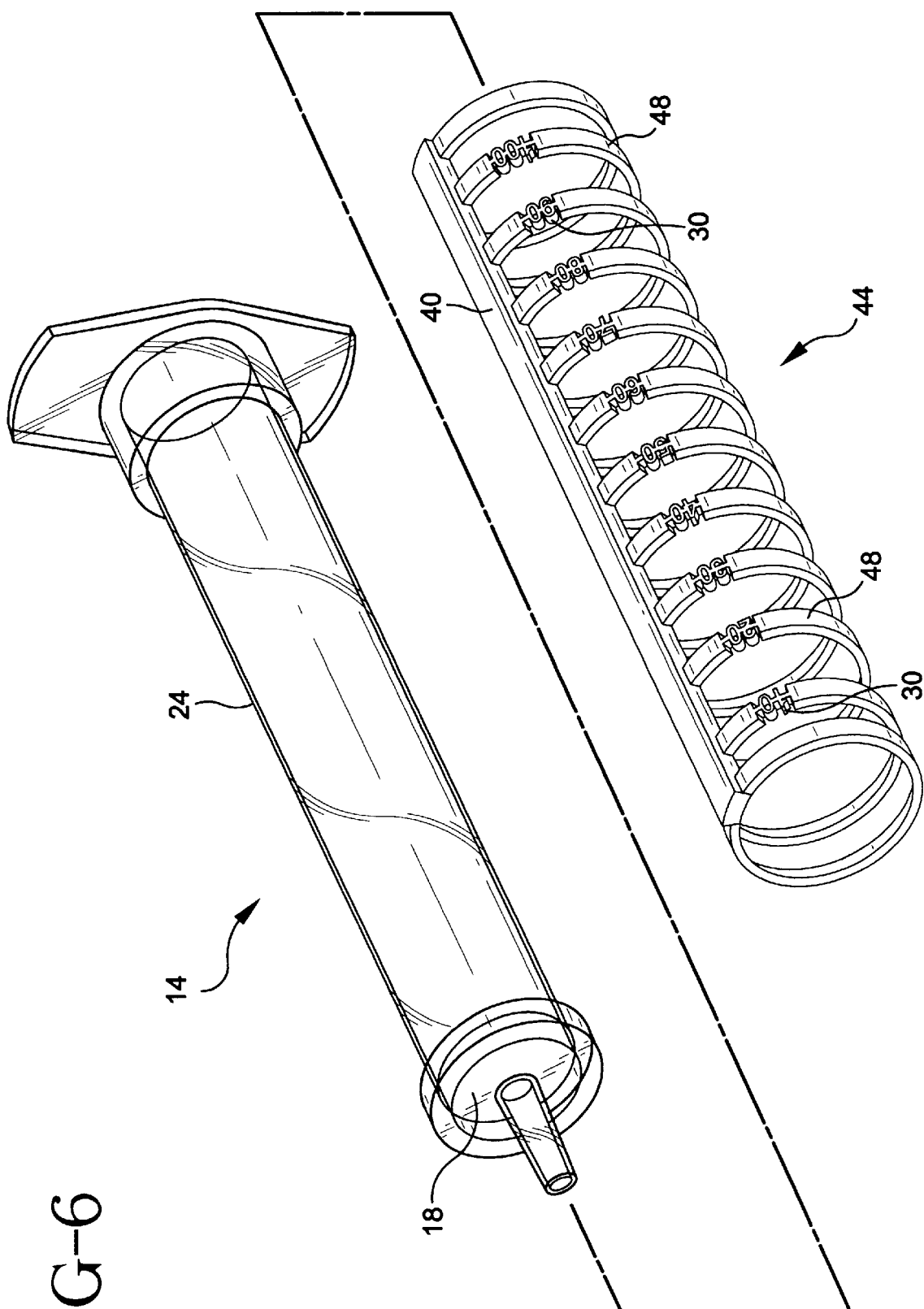
FIG. 6 is an exploded perspective view of FIG. 1 illustrating an alternative method of assembly.

Adverting to FIGS. 1–2, a syringe barrel 12 is illustrated having an improved scale 44. Syringe barrel 12 in FIGS. 1 and 3 comprise an elongated barrel 18 having an inner surface 20 and an outer surface 24. Inner surface 20 defines a chamber 28 for retaining fluid. Inner surface 20 and outer surface 24 are transparent. Improved scale 44 in FIG. 1 has a scale bar 40, scale marks 48, and indicia 30. Improved scale 44 is integrally formed into outer surface 24 and is a structural part of outer surface 24 such that inner surface 20 is substantially uninterrupted by improved scale 44. Scale bar 40 is formed axially along outer surface 24 as shown in FIG. 1. Scale marks 48 and indicia 30 are formed from about 1° to 360° circumferentially around syringe barrel 12. Indicia 30 are volume measuring indicia. Improved scale 44 can be made of various materials offering different colors such as a color selected from the group consisting of white, black, yellow, red, blue, green and combinations thereof. Preferably, improved scale 44 is made of an elastomeric material. However, it can be made of any thermoplastic material or injection-molded material. Syringe barrel 12 and alternate syringe barrel 14 has improved scale 44 substantially embedded into outer surface 24 as illustrated in FIGS. 5–6. FIG. 3 demonstrates improved scale 44 protruding outwardly from outer surface 24. Improved scale 44 in both embodiments provides tactile sensation or readability of the scale 44 and slip resistant holding of syringe barrel 12 by its having scale 44 protruding outwardly. The tactile readability yields a braille-like sensation on the scale 44. Scale bar 40 is also protruding outwardly and provides contrast to the liquid in chamber 28 as well as support to scale marks 48 and indicia 30. Scale bar 40 also provides slip resistant holding.

Improved scale 44 can be formed by co-injection molding, heat welding and overmolding processes. Preferably, improved scale 44 is formed by co-injection molding. The advantage of using one of these processes is to accurately and permanently position improved scale 44. In addition, secondary operations are eliminated saving time and cost from the assembly procedure. FIG. 3 and FIG. 5 illustrate co-injection molding and heat-welding processes. In a co-injection molding process, elongate barrel 18 is molded with inner 20 and outer surfaces 24. Improved scale 44 is simultaneously molded on outer surface 24. In a heat-welding process, elongate barrel 18 is molded with inner 20 and outer surfaces 24. Improved scale 44 is molded with inner 52 and outer surfaces 54. Inner surface 54 of improved scale 44 is then heat-welded on outer surface 24 of elongate barrel 18.

FIG. 6 illustrates improved scale 44 being made by overmolding. It is preferred for this method in molding improved scale 44 to have a scale bar 40, scale marks 48 and indicia 30. In this embodiment, an alternate syringe barrel 14 forms an elongate barrel 18 around improved scale 44 wherein improved scale 44 is integrally formed into elongate barrel 18. This process also provides a syringe with tactile readability and slip resistant holding. In addition, it provides a method to accurately and permanently position improved scale 44. Thus, secondary operations, such as printing, is eliminated. This method also allows different material to be used for improved scale 44 and allows improved scale 44 to be from about 1° to 360° around the syringe barrel 14. In addition, the scale bar 40 provides contrast to liquid in elongated barrel 18.

There are a number of different methods that achieve multi-material molding in addition to the ones described. Some of the most widely used methods include co-injection, overmolding, two-shot molding, and sandwich molding. In all cases, the basic premise of multi-material molding is to take economical advantage of two or more materials with uniquely different properties by incorporating them into one molded component. (See K. A. Kerouac et. al., "Innovative Injection Molding Techniques for the Medical Industry", *Medical Device & Diagnostic Industry*, April 1998, Canon Publishing, pp. 67–68)

In co-injection and sandwich molding, parts are formed with the skin of one material and a core or another. The critical material requirement in this kind of molding is compatibility. If the two polymers are not compatible, they will not adhere to each other, resulting in delamination at the interface between the two polymer layers and failure of the part.

In co-injection molding, two barrels are joined together by a common manifold and nozzle, through which both materials flow before entering the mold cavity. On injection of the molten plastic, the injection unit with the skin material (often called the A-barrel or A-side) injects the set amount of polymer. This is followed by the core material in the B-barrel, which penetrates the skin polymer and completes filling of the cavity without breaking through the skin surface. Since plastic flow in injection molding is laminar, the two materials can be molded in the skin/core configuration without mixing with each other.

Co-injection molding often has a third stage, in which a small amount of skin material completes the injection stage. This is known as an A-B-A-injection sequence. This sequence accomplishes the task of completely encapsulating the core material. Thus, protection from weathering, chemicals or other environmental hazards can be attained.

Sandwich molding also results in a skin/core structure, but the mechanics are slightly different. In this process, multiple plasticating units are used only as extruders to feed their percentage of the total shot to a single injection unit. The injection unit itself also accounts for one of the polymer layers. Prior to injection, the injection unit has built up a shot consisting of as many layers as there are materials. Again, because of the laminar nature of the polymer flow in the injection molding process, these layers do not mix with each other. Upon injection, the last material fed into the injection unit, which is at the front of the barrel, becomes the skin of the part. All of the subsequent layers form beneath it, working toward the center until the last material (which was that material plasticated by the injection unit itself) becomes the core. Because all of the injection is done through only one injection unit there is no opportunity for an A-B-A-sequence as in co-injection. Therefore, complete encapsulation of the core is not possible. The core will be exposed at the gate leading to the cavity which is often not a problem if the gate is in an area of the part that will be hidden or if the material of the core is resistant to the detrimental effects of environmental chemical exposure. (See Id.)

Both these processes can attain a part with surface features such as a soft touch which has a rigid core material and a soft outer shell.

Another process is called overmolding. With sandwich or co-injection molding it may not always be apparent that two materials are being used. Overmolding or two-shot molding results in parts in which it is clearly evident that more than one material is being used. In these processes, only part of the product is molded in one material, and that molded piece is manipulated so that the second material can be molded around, over, under or through to complete the final part. This method is sometimes referred to as in-mold assembly. In most cases, good compatability of different materials is required to promote good adhesion and to prevent delamination and part failure. However, incompatible materials may be deliberately molded with each other for applications in which relative motion between the two sub-components is desired. It is possible, for instance, to create a joint part with a ball molded in one material and a socket molded in a second, incompatible material. The incompatible, the ball and socket will not adhere. Thus, an allowance of free movement between the two components can be accomplished. The primary benefit of overmolding, as in co-injection and sandwich molding, is a saving on assembly and secondary operations cost. Downstream secondary operations may be eliminated, and time and expense are reduced if these methods are used. (See Id.)

Heat welding is another process that can be used to obtain the desired result of the present invention. Using this process, both components are injection molded separately. When the parts are completely formed, one component may be heated above its glass transition temperature and is placed over the other part or in the other part and quickly cooled to a temperature below the glass transition point of the heated material. This temperature change allows the heated plastic material to solidify and weld on the other plastic part. Thus common adherence is attained at the surface of both materials.

Figure 4:
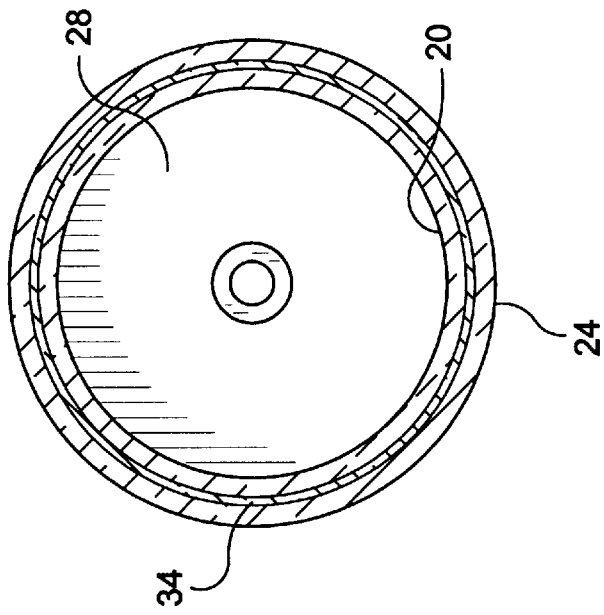
FIG. 4 is a cross-sectional view of the syringe barrel with an improved scale of FIG. 2 taken along lines 4—4.
Figure 7:
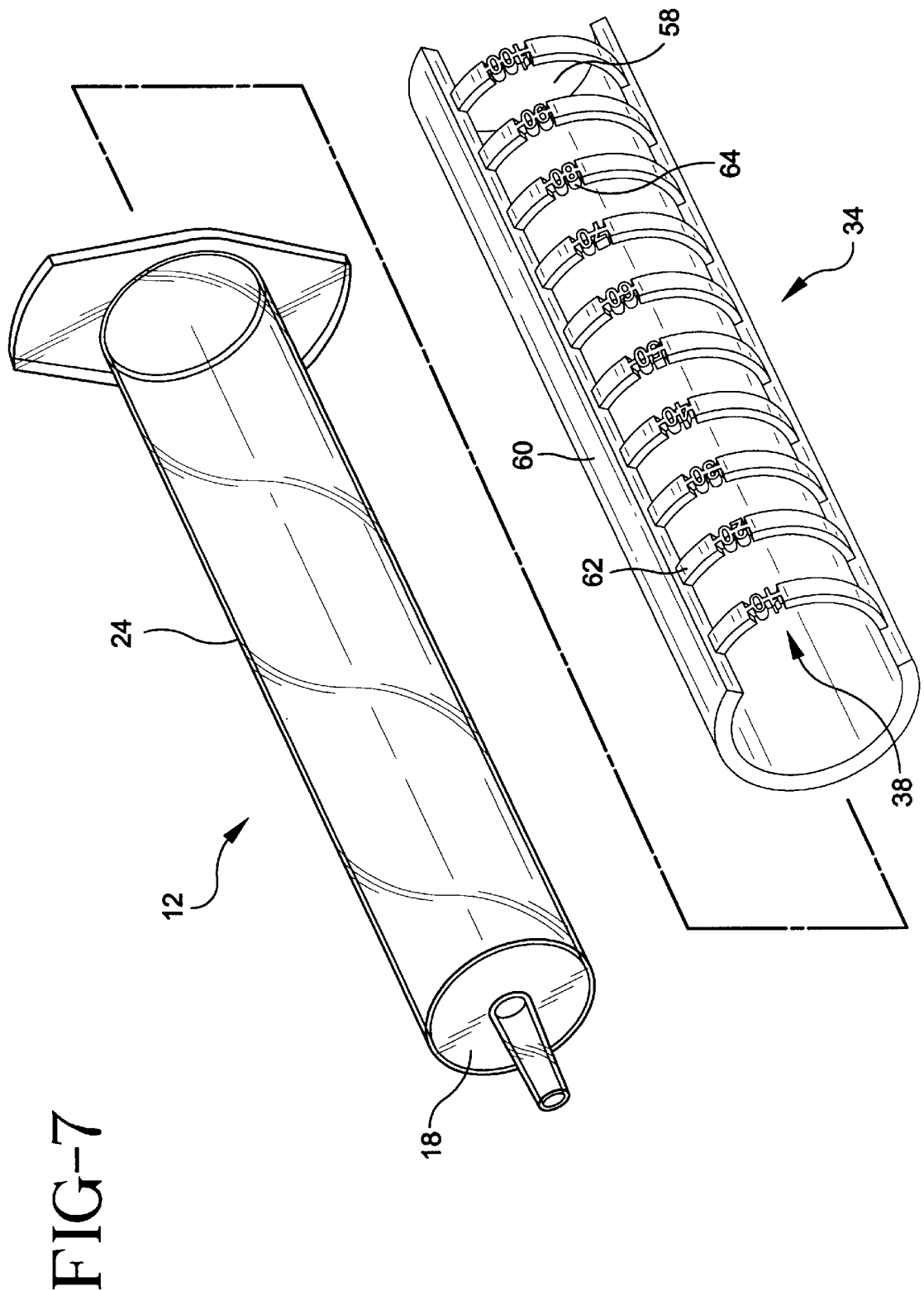
FIG. 7 is an exploded perspective view of an alternative embodiment.

An alternate embodiment is shown in FIG. 2, FIG. 4 and FIG. 7. FIG. 2 and FIG. 4 illustrate syringe barrel 12 having inner 20 and outer surfaces 24. Inner surface 20 defines a chamber 28 for retaining fluid. Inner surface 20 and outer surface 24 are transparent. A tubular foil 34 has transparent portions 58 as shown in FIG. 7. Tubular foil 34 has an improved scale 38 formed thereon. Improved scale 38 has a scale bar 60, scale marks 62 and indicia 64. The scale bar 60 is not required for the present invention to provide the scale 38 to 360° around the syringe barrel 12. However, scale bar 60 does provide contrast to liquid in the syringe barrel 12. Tubular foil 34 as shown in FIG. 4 and FIG. 2 is integrally formed between inner surface 20 and outer surface 24 of elongate barrel 18. Thus, in this alternate embodiment tactile sensation or readability of scale 38 and slip resistant holding of syringe barrel 12 is not advanced. However, accurately and permanently placing the scale 38 and eliminating a secondary operation is available by this embodiment through the disclosed processes. In addition, the ability to mold the scale 38 to 360° is available by this embodiment. Different thermoplastic materials can be used in this embodiment.

Tubular foil 34 is made of a thermoplastic material and can be extruded or injection molded. If tubular foil 34 is extruded, improved scale 38 can be made by a die cut method. Indicia 64 are volume measuring indicia. Improved scale 38 can be made of material being a color selected from the group consisting of white, black, yellow, red, blue, green and combinations thereof. Different thermoplastic materials can be used in this embodiment. Scale marks 62 and indicia 64 are formed from about 1° to 360° circumferentially around elongate barrel 18. The method of overmolding previously described can be used to form improved scale 38. In this over-molding process, improved scale 44 is replaced with tubular foil 34 which contains improved scale 38. Preferably, improved scale 38 contains scale marks 62, and indicia 64. However the scale bar 60 can be used to provide contrast to scale 39. Indicia 64 are volume measuring indicia. The advantage to this process is to eliminate the secondary operation of printing and allow improved scale 44 to be formed to 360° around elongated barrel 18. This characteristic is difficult to obtain using conventional printing methods.

What is claimed is:

1. A syringe barrel comprising:

an elongated barrel having inner and outer surfaces, said inner surface defining a chamber for retaining fluid, said inner and said outer surface being transparent;

a scale having scale marks and indicia, said scale integrally molded into said outer surface and immovably attached to said barrel, said scale being a structural part of said outer surface such that said inner surface is substantially uninterrupted by said scale; and said scale marks and indicia protruding outwardly from said outer surface for providing tactile sensation of said scale marks and indicia and slip resistant holding of the syringe barrel.

2. The syringe barrel of claim 1, wherein said scale further comprises a scale bar formed axially along said outer surface for providing additional support to said scale marks and indicia and for providing contrast to said scale.

3. The syringe barrel of claim 1, wherein said scale marks and said indicia are formed from about 1° to 360° circumferentially around the syringe barrel.

4. The syringe barrel of claim 1, wherein said indicia comprises volume measuring indicia.

5. The syringe barrel of claim 1, wherein said scale is made of material being a color selected from the group consisting of white, black, yellow, red, blue, green and combinations thereof.

6. The syringe barrel of claim 1, wherein said scale is made of an elastomeric material.

7. The syringe barrel of claim 1, wherein said scale is made of a thermoplastic material.

8. The syringe barrel in claim 1, wherein said scale is formed by a co-injection molding process.

9. The syringe barrel in claim 1, wherein said scale is formed by a heat-welding process.

10. The syringe barrel in claim 1, wherein said scale is formed by an overmolding process.

11. A syringe barrel comprising:

an elongated barrel having inner and outer surfaces, said inner surface defining a chamber for retaining fluid, said inner and said outer surface being transparent;

a scale having a scale bar, scale marks and indicia, said scale bar formed axially along said outer surface for providing structural support to said scale marks and said indicia and for providing contrast to said scale, said scale integrally molded into said outer surface and immovably attached to said barrel, said scale being a structural part of said outer surface such that said inner surface is substantially uninterrupted by said scale;

said scale marks and said indicia are formed from about 1° to about 360° circumferentially around the syringe barrel; and said scale marks and indicia protruding outwardly from said outer surface for providing tactile sensation of said scale marks and indicia and slip-resistant holding of the syringe.

12. The syringe barrel of claim 11, wherein said indicia comprise volume measuring indicia.

13. The syringe barrel of claim 11, wherein said scale is made of an elastomeric material.

14. The syringe barrel of claim 11, wherein said scale is made of a thermoplastic material.

15. The syringe barrel of claim 11, wherein said scale is made of material being a color selected from the group consisting of white, black, yellow, red, blue, green and combinations thereof.

16. A syringe barrel comprising:

an elongated barrel having inner and outer surfaces, said inner surface defining a chamber for retaining fluid, said inner and said outer surfaces being transparent;

a scale having a scale bar, scale marks and indicia, said scale bar formed axially along said outer surface for providing structural support to said scale and said indicia and for providing contrast to said scale, said scale made of an elastomeric material and integrally molded into said outer surface and immovably attached to said barrel, said scale being a structural part of said outer surface such that said inner surface is substantially uninterrupted by said scale;

said scale marks and said indicia are formed from about 1° to about 360° circumferentially around the syringe barrel;

said scale formed by a co-injection molding process for eliminating secondary printing operations; and said scale marks and indicia protruding outwardly from said outer surface for providing tactile sensation of said scale marks and indicia and slip-resistant holding of the syringe.

17. A syringe barrel comprising:

an elongated barrel having inner and outer surfaces, said inner surface defining a chamber for retaining fluid, said inner surface and said outer surface being transparent;

a tubular foil having transparent portions, and a scale formed thereto, said scale having scale marks indicia, said tubular foil integrally molded and immovably attached between said inner surface and said outer surface of said elongate barrel such that said inner surface is substantially uninterrupted by said foil;

said scale marks and said indicia are formed from about 1° to about 360° circumferentially around said elongate barrel; and said scale is formed by an over-molding process for eliminating secondary printing operations.

18. The syringe barrel of claim 17, wherein said tubular foil further comprises a scale bar for providing contrast to said scale.

19. The syringe barrel of claim 17, wherein said tubular foil is formed by an extrusion process.

20. The syringe barrel of claim 17, wherein said tubular foil is formed by an injection molding process.

21. The syringe barrel of claim 17, wherein said indicia comprises volume measuring indicia.

22. The syringe barrel of claim 17, wherein said scale is made of material being a color selected from the group consisting of white, black, yellow, red, blue, green and combinations thereof.

* * * * *